United States Patent
Huang et al.

(10) Patent No.: US 10,076,331 B2
(45) Date of Patent: Sep. 18, 2018

(54) DEVICE AND METHOD FOR FORMING AN ANASTOMOTIC JOINT BETWEEN TWO PARTS OF A BODY

(71) Applicants: Nanyang Technological University, Singapore (SG); Tan Tock Seng Hospital Pte Ltd, Singapore (SG)

(72) Inventors: Yingying Huang, Singapore (SG); Subramanian Venkatraman, Singapore (SG); Sing Joo Chia, Singapore (SG)

(73) Assignees: Nanyang Technological University, Singapore (SG); Tan Tock Seng Hospital PTE Ltd, Singapore (SG)

( * ) Notice: Subject to any disclaimer, the term of this patent is extended or adjusted under 35 U.S.C. 154(b) by 228 days.

(21) Appl. No.: 14/765,091

(22) PCT Filed: Jan. 28, 2014

(86) PCT No.: PCT/SG2014/000038
§ 371 (c)(1),
(2) Date: Jul. 31, 2015

(87) PCT Pub. No.: WO2014/120092
PCT Pub. Date: Aug. 7, 2014

(65) Prior Publication Data
US 2015/0359537 A1     Dec. 17, 2015

Related U.S. Application Data

(60) Provisional application No. 61/759,642, filed on Feb. 1, 2013.

(51) Int. Cl.
*A61B 17/08* (2006.01)
*A61B 17/11* (2006.01)
(Continued)

(52) U.S. Cl.
CPC ........... *A61B 17/11* (2013.01); *A61B 17/1114* (2013.01); *A61B 90/39* (2016.02);
(Continued)

(58) Field of Classification Search
CPC ...... A61B 17/0057; A61B 2017/00575; A61B 2017/00588; A61B 2017/00592;
(Continued)

(56) References Cited

U.S. PATENT DOCUMENTS 5,035,702 A      7/1991  Taheri
9,295,456 B2 *   3/2016  Subramanian ..... A61B 17/0057
(Continued)

FOREIGN PATENT DOCUMENTS

WO     WO 97/27898 A1     8/1997
WO     WO 97/47254 A1     12/1997
(Continued)

OTHER PUBLICATIONS

Dictionary.com definition of "near" as accessed Dec. 1, 2017; http://www.dictionary.com/browse/near.*
(Continued)

*Primary Examiner* — Jonathan Miles
(74) *Attorney, Agent, or Firm* — Alston & Bird LLP

(57) ABSTRACT

A device and method for forming an anastomotic joint between two parts of a human or animal body having a hollow connector with at least two proximal arms biased towards an open position; and at least two distal arms biased towards an open position, wherein in use when pressure is applied to the proximal arms to overcome the bias into a position in which the proximal arms are closer to each other; similarly pressure is applied to the distal arms to overcome the bias into a position in which the distal arms are closer to each other; the distal end can be pushed into a passage in the first human or animal body part until the distal arms are
(Continued)

located in the first lumen of the first body part and released allowing the distal arms to move to the biased position to urge against the first lumen of the first body part; and the proximal end can be pushed into a passage in the second human or animal body part until the proximal arms are located in the second lumen of the second body part and released allowing the proximal arms to move to the biased position to urge against the second lumen of the second body part.

16 Claims, 9 Drawing Sheets

(51) Int. Cl.
    *A61B 90/00*     (2016.01)
    *A61B 17/00*     (2006.01)

(52) U.S. Cl.
    CPC ........... *A61B 2017/00004* (2013.01); *A61B 2017/00884* (2013.01); *A61B 2017/00893* (2013.01); *A61B 2017/1107* (2013.01); *A61B 2017/1132* (2013.01); *A61B 2017/1135* (2013.01); *A61B 2090/3966* (2016.02)

(58) Field of Classification Search
    CPC ........... A61B 2017/00597; A61B 2017/00615; A61B 2017/00606; A61B 17/11; A61B 2017/1107; A61B 17/1114; A61B 2017/1132; A61B 2017/1135; A61B 2017/1139; A61F 2/01; A61F 2002/016; A61F 2002/018
See application file for complete search history.

(56) References Cited

U.S. PATENT DOCUMENTS

| | | |
|---|---|---|
| 2003/0088256 A1 | 5/2003 | Conston et al. |
| 2006/0004393 A1 | 1/2006 | Amarant |
| 2007/0179527 A1* | 8/2007 | Eskuri ............... A61B 17/0057 606/213 |

FOREIGN PATENT DOCUMENTS

| | | | |
|---|---|---|---|
| WO | WO 2004/087236 A2 | 10/2004 | |
| WO | WO 2009/046126 A1 | 4/2009 | |
| WO | WO 2011/096896 A1 * | 8/2011 | ......... A61B 17/0057 |

OTHER PUBLICATIONS

Extended European Search Report from corresponding European Patent Application No. 14746630.4, dated Sep. 21, 2016.
International Search Report and Written Opinion for corresponding International Application No. PCT/SG2014/000038, dated Mar. 24, 2014.

* cited by examiner

DEVICE AND METHOD FOR FORMING AN ANASTOMOTIC JOINT BETWEEN TWO PARTS OF A BODY

This application claims the benefit of priority of U.S. Provisional. Patent Application No. 61/759,642 filed Feb. 1, 2013, the contents of which being hereby incorporated by reference in its entirety for all purposes.

FIELD

The invention relates to devices or methods for forming an anastomotic joint between two parts of a body

BACKGROUND

An anastomotic joint is the connection between two body vessels that allow fluids to pass between the two body vessels. Essentially, an anastomotic joint is a communicating opening. Examples of natural anastomotic joints include the connection between the bladder and the urethra, between blood vessels, and the junctions at the different segments of the gastrointestinal track.

Surgical anastomosis is a man made connection between two body structures. It usually means a connection that is created between tubular structures, such as blood vessels, loops of intestine, or ureteral tract. Often surgical anastomosis is conducted to reconnect parts of the body that should be in fluid contact, for example where a segment of the intestine is resected the two remaining ends are rejoined. Similarly, as the prostate surrounds the upper urethra removal of the prostate will require reconnection of the bladder and the urethra. In addition to the open surgery, a few new types of surgery such as laparoscopic prostatectomy and robotic-assisted prostatectomy were also developed in recent years. However, removal of the prostate leaves a gap between the urethra and the bladder neck. The present practice for anastomosis is hand sewing or robotic arm sewing. Not only is this procedure technically difficult, it requires about 45 minutes operating time for clinicians, whereby the connection is unstable, insecure and increases the risk of infection requiring longer external catheterization of the patient. The patient needs to be cathatarised to avoid the fluid passage between the two body parts coming into contact with the sutured wound before is has a chance to grow together and heal.

Surgical anastomosis is technically difficult; an issue known in 1902 when Alexis Carrel formulated four main guidelines for surgical anastomosis: 1) avoid luminal narrowing at the anastomotic site, 2) avoid the creation of folds and a rough inner surface of the vessel, 3) a need to oppose the two intimal edges closely, and 4) eliminating contact of suture material with blood.

After 100 years, the needle and thread are still used for the anastomosis. Suturing, however, has several detrimental aspects. The penetrating needle induces vascular/organ wall damage, which influences the healing response. The patient needs to be cathatarised to avoid the fluid passage between the two body parts coming into contact with the sutured wound before is has a chance to grow together and heal. Although, many attempts have been made to reduce the damage to the wall by using non-absorbable suture materials (cotton, nylon, stainless steel), absorbable sutures (catgut, polyglycolic acid, polydioxanone, polyglactin), or the atraumatic needle it is difficult to minimize wall damage. Currently, the only way to reduce or minimize wall damage is by the surgeons skill which is highly individualistic and damage cannot be eliminated entirely by such means.

An object of the invention is to ameliorate at least some of the problems listed above.

SUMMARY

Accordingly, a first aspect of the invention relates to a device for forming an anastomotic joint between two parts of a human or animal body comprising: a hollow connector having connected near a proximal end of the connector at least two proximal arms each of which has a free end, wherein at least portions including the respective free ends of these at least two proximal arms are movable or rotatable or foldable with regard to each other between positions in which the free ends of said proximal arms are closer to each other and positions in which the distance between the free ends of said proximal arms is comparably larger, and wherein these at least two proximal arms are biased towards respective directions in which the respective free ends of said proximal arms are movable to respective positions in which the distance between said free ends of said proximal arms is enlarged, so that the proximal arms are configured to urge against an inner wall surface of a first lumen of a first human or animal body part so as to anchor the connector to said first human or animal body part; and having connected at least two distal arms connected near a distal end of the connector each of which distal arms has a free end, wherein at least portions including the respective free ends of these at least two distal arms are movable or rotatable or foldable with regard to each other between positions in which the free ends of said distal arms are closer to each other and positions in which the distance between the free ends of said distal arms is comparably larger, and wherein these at least two distal arms are biased towards respective directions in which the respective free ends of said distal arms are movable to respective positions in which the distance between said free ends of said distal arms is enlarged, so that the distal arms are configured to urge against an inner wall surface of a second lumen of a second body part so as to anchor the connector to said second human or animal body part.

Another aspect of the invention relates to a method of forming an anastomotic joint between two parts of a human or animal body using a device of claim 1 comprising:
 a) Providing pressure to move the proximal arms into a position in which the free ends of said proximal arms are closer to each other;
 b) Providing pressure to move the distal arms into a position in which the free ends of said distal arms are closer to each other;
 c) Pushing the device using the distal end leading into a passage in the first human or animal body part until the distal arms are located in the first lumen of the first body part;
 d) Releasing the pressure on the distal arms allowing them to move to the biased position in which the respective free ends of distal arms is at an enlarged distance to urge against the first lumen of the first body part;
 e) Pushing the device using the proximal end leading into a passage in the second human or animal body part until the proximal arms are located in the second lumen of the second body part; and
 f) Releasing the pressure on the proximal arms allowing them to move to the biased position in which the respective free ends of said proximal arms is at an enlarged distance to urge against the second lumen of the second body part.

Other aspects of the invention would be apparent to a person skilled in the art with reference to the following drawings and description of various non-limiting embodiments.

BRIEF DESCRIPTION OF THE DRAWINGS

The drawings are not necessarily drawn to scale, emphasis instead generally being placed upon illustrating the principles of various embodiments. In the following description, various embodiments of the invention are described with reference to the following exemplary drawings.

DETAILED DESCRIPTION

Figure 1:
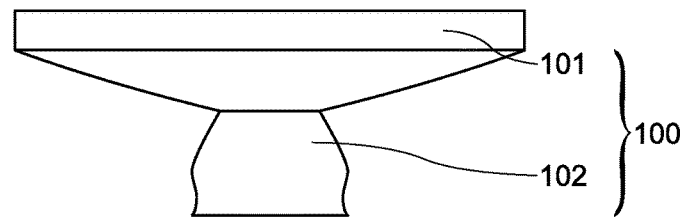
FIG. 1: is a schematic diagram showing a comparison between (A) connected state of, two hollow parts of the body in the form of a natural anastomotic joint and (B) disconnected state of two hollow parts of the body.
Figure 1:
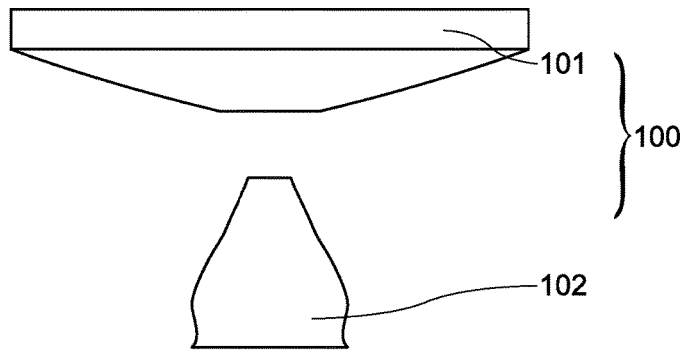

The key concept involves using a 'connector' instead of the current stitching to create an artificial anastomotic joint of body ducts, vessels, organs, and other structures, collectively body lumens.

Accordingly, a first aspect of the invention relates to a device for forming an anastomotic joint between two parts of a human or animal body comprising: a hollow connector having connected near a proximal end of the connector at least two proximal arms each of which has a free end, wherein at least portions including the respective free ends of these at least two proximal arms are movable or rotatable or foldable with regard to each other between positions in which the free ends of said proximal arms are closer to each other and positions in which the distance between the free ends of said proximal arms is comparably larger, and wherein these at least two proximal arms are biased towards respective directions in which the respective free ends of said proximal arms are movable to respective positions in which the distance between said free ends of said proximal arms is enlarged, so that the proximal arms are configured to urge against an inner wall surface of a first lumen of a first human or animal body part so as to anchor the connector to said first human or animal body part; and having connected at least two distal arms connected near a distal end of the connector each of which distal arms has a free end, wherein at least portions including the respective free ends of these at least two distal arms are movable or rotatable or foldable with regard to each other between positions in which the free ends of said distal arms are closer to each other and positions in which the distance between the free ends of said distal arms is comparably larger, and wherein these at least two distal arms are biased towards respective directions in which the respective free ends of said distal arms are movable to respective positions in which the distance between said free ends of said distal arms is enlarged, so that the distal arms are configured to urge against an inner wall surface of a second lumen of a second body part so as to anchor the connector to said second human or animal body part.

The hollow connecter allows passage of fluid with no possibility of leaks or infection while the two body parts grow together. As such, there would be no need for a temporary external catheterization since the internal connector serves to improve the healing of anastomosis, as well as to drain fluid.

The proximal arms 41 biased in a position in which the free ends of said proximal arms are at a distance far from each other are refered to herein as being biased in an open position and the distal arms 11 biased in a position in which the free ends of said distal arms are at a distance far from each other are refered to herein as being biased in an open position allow the device to be quickly deployed to connect two parts of the body while providing a fluid through passageway between the lumen of the first body part and the lumen of a second body part with minimal damage to the vascular/organ walls. This will improve the healing of the anastomosis in the gap between the two tubular hollow parts of body, completely eliminating the hand sewing step which is technically difficult and time consuming, as well as minimize the risk of infection. The lumen refers to the hollow inside space of a vessel or an organ of the body.

The arms 41, 11 may be biased by using of an elastomer at the join 4 between the connector 2 and the arms 41, 11. The elastomer may comprise any suitable amphorous or semi-crystal polymer existing above its glass transition temperature such that, considerable segmental motion is possible. The elastomer is configured to hold the arms in an open configuration at an angle between about 10 degrees and about 90 degrees in relation to the connector 2, preferably the arms are biased at an angle between about 60 and about 85 degrees, more preferably about 70 to 80 and most preferably about 75 degrees in relation to the connector. The flexibility of the elastomer will allow the arms 41, 11 to be movable or rotatable or foldable from the open position in which the free ends of said arms are at a distance far from each other towards the hollow connector 2 such that the arms 41, 11 can be pushed flat or parallel along the hollow connector 2 via pressure but they will return to the biased configuration when the pressure is removed. This feature allows self-expandability of the arms by using a unique flap design made of elastomer with high recoverability.

The proximal arms 41 or the distal arms 11, or both sets of at least two arms 41, 11 may independently from each other, comprise three or more arms outwardly extending from the connector 2 as the at least two arms. The arms 41, 11 may be connected to the connector 2. The arms may be movable or rotatable or foldable and may, thus, be adapted to be folded at their inner ends of the arms where they are connected to the hollow connector. Thereby, the arms may be folded inwardly or outwardly against the connector 2 to be pushed flat or parallel along the hollow connector 2 in either direction.

The term "proximal", also referred herein as "bottom part" or "bottom" of the connector, refers to a location that in use is closest to the gap that is to be connected by the device. The term "distal", also referred herein as "top part" or "top" of the connector, on the other hand, refers to a location furthest from the gap that is to be connected by the device. Furthermore, in various embodiments, the proximal arms downwardly extends from the proximal junction end, or may upwardly extends from the proximal junction end; while the distal arms downwardly extends from the distal junction end, or may upwardly extends from the distal junction end.

In various embodiments, the hollow connector 2 may be integrally provided together with the arms 41, 11, the arms being movable or rotatable or foldable. Therefore, the arms are adapted to resist high mechanical stress.

The form of the arms 41, 11 or spokes is generally like a rod having a rounded or any other cross section, such as square, rectangular, hexagonal, octagonal or triangular. "Rounded" means in the context of the present application, that the at least two arms can have a circular cross section or an oval cross section. The edging of the arms or spokes can be rounded.

In various embodiments the hollow connector 2 may be integrally provided. This may be suitable for embodiments in which the device is formed from the same polymeric material, where polymer processing methods such as cast molding, injection molding, compression molding, machining, laser cutting and combination of above methods may be used to form the device. In alternative embodiments, it may be suitable to prepare separate parts of the device from different polymeric materials to specifically adjust the required performance of the material.

In various embodiments the hollow connector comprises two interconnecting parts, a proximal connector portion (proximal juction portion) 20 and a distal connector portion (distal juction portion) 30. The advantage of the device comprising the hollow connector 2 in two interconnecting parts, is that the two smaller portions can, more easily be moved around the body especially where small body parts are to be joined.

In various embodiments a surface of an inner wall 32 of the distal connector portion 30 comprises grooves patterned on the surface; and a surface of an outer wall 22 of the proximal connector portion 20 comprises projections patterned on the surface whereby the projections are able to interlock with the grooves forming the interconnected parts of the hollow connector 2. Any suitable interlock known in the art would be suitable as long as the proximal junction portion 20 can form a firm connection with the distal junction portion 30. The artificial joining of the two interconnected parts acts in the same way as suturing but it is far less time consuming and meets the requirements set out by Alexis Carrel in 1902 while eliminating the sewing step. In various embodiments the grooves are a thread track and the projections are a thread whereby the two parts are interconnected by screwing the proximal connector portion and the distal connector portion together. In various other embodiments the grooves are sleeves and the projections are expansion-bolts whereby the two parts are interconnected by forcing the proximal connector portion over the distal connector portion.

In various embodiments, the proximal junction portion 20 may be a tube, such as a polymeric tube, adapted to receive the joint of the proximal arms 11 from its proximal end. The distal junction portion 30 may be a tube, such as polymeric tube, adapted to receive the joint of the distal arms 41 from its distal end. The junction portion may have a length of between about 1 to 20 mm, for example, about 1, 2, 3, 4, 5, 6, 7, 8, 9, 10, 11, 12, 13, 14, 15, 16, 17, 18, 19 or 20 mm. The junction portion may be, a tube having a diameter of about 3 to 10 mm, for example, about 3, 4, 5, 6, 7, 8, 9, or 10 mm. The wall thickness of the tube, may be between about 0.5 to 3 mm, for example, about 0.5, 0.6, 0.7, 0.8, 0.9, 1, 2, or 3 mm.

The proximal junction portion 20 and the distal junction portion 30 may be a tube with structured surface; the surface may be the exterior surface or interior surface. If, the proximal junction portion 20 has the exterior surface, the distal junction portion 30 correspondingly has the interior surface and vice verse, such the if the proximal junction portion 20 has the interior surface, the distal junction portion 30 correspondingly has the exterior surface.

In various embodiments, the proximal structured exterior surface 22 may be the expansion-bolts chamfered structure, the structured sleeve 32, may distribute on the one layer of peripheral exterior surface of the proximal hollow tube 20. The number of sleeves can include at least 2 or more sleeves as long as the proximal junction portion 20 can form a firm connection with the distal junction portion 30. The structure sleeve may distribute on the one layer or more layers on the longitudinal direction of the exterior surface of the hollow tube. In case of the proximal structured exterior surface is the expansion-bolts chamfered structure, the distal structured interior surface may be the anchor chamfered shell structure. The number of shell layer can include at least 1 or more layers as long as the proximal structured exterior surface can anchor and form the firm connection with the distal structured interior surface.

The number of sleeves is not limited as long as the proximal junction portion 20 can form the firm connection with the distal junction portion 30. For example, in case the proximal junction portion comprises a proximal hollow tube and a expansion bolt chamfered structured exterior surface, the number of sleeves can include 2 or more sleeves as long as the proximal junction portion 20 can form the firm connection with the distal junction portion 30. The exterior surface may include, but are not limited to 2 to 8 sleeves in one peripheral layer, such as 2, 3, 4, 5, 6, 7, or 8 sleeves. In various embodiments, the number of the sleeves in the one peripheral layer is 4. The peripheral layer may be at least 1 or more layers in the longitudinal direction of the proximal hollow tube. The number of the sleeve layers in the proximal junction portion may be same or different with the number of the shell layers in the distal junction portion 30. In various embodiments, the number of the sleeve layers in the proximal junction portion 20 is more than the number of the shell layer in the distal junction portion 30.

The form of the sleeve is generally like a rod having triangular or any other cross section, such as square, rectangular, hexagonal, or octagonal.

In various embodiments the device is formed from a biodegradable polymer. Using a biodegradable polymer will not require the device to latter be removed after the two body parts have naturally grown and fused together. The connector in this case is fully degradable. This will improve the healing of the anastomosis in the gap between the two tubular hollow parts of body. The biodegradable connector allows for post-surgical management of anastomosis.

The terms "bioabsorbable", "biodegradable" and "bioresorbable" are used interchangeably herein, and refers to the ability of a material to degrade or breakdown over a period of time due to the chemical and/or biological action of the body. In the context of the present invention, the term "biodegradable polymer" refers to a polymer comprising one or more polymeric components that can be completely removed from a localized area by physiological metabolic processes such as resorption. For example, a biodegradable polymer may, when taken up by a cell, be broken down into smaller, non-polymeric subunits by cellular machinery, such as lysosomes or by hydrolysis that the cells can either reuse or dispose of without significant toxic effect on the cells. Examples of biodegradation processes include enzymatic and non-enzymatic hydrolysis, oxidation and reduction. Suitable conditions for non-enzymatic hydrolysis, for example, include exposure of biodegradable material to water at a temperature and a pH of a lysosome (i.e. the intracellular organelle). The degradation fragments typically induce no or little organ or cell overload or pathological processes caused by such overload or other adverse effects in vivo.

Various examples of biodegradable polymer materials are known in the art, any of which are generally suitable for use as the biodegradable polymer of the present invention. Examples of polymers that are considered to be biodegradable include aliphatic polyesters, poly(amino acids), copoly (ether-esters), polyalkylenes oxalates, polyamides, poly (iminocarbonates), polyorthoesters, polyoxaesters, polyamidoesters, polyoxaesters containing amido groups, poly(anhydrides), polyphosphazenes, polycarbonates, naturally-occurring biodegradable polymers such as chitosan, collagen, starch, and blends thereof. Examples of polyortho esters include a polylactide, a polyglycolide, a polycaprolactone, a polylactic acid, a biodegradable polyamide, a biodegradable aliphatic polyester, and/or copolymers thereof, or with other biodegradable polymers such as those mentioned above.

Most bioabsorbable polymers available today, such as polylactic acids (PLA), polycaprolactone (PCL) and poly-lactic-co-glycolic acid (PLGA) display a very similar mechanical behavior, with a high Young's modulus and rather low elongation at break values. Sometimes these polymers seem in a pure form inappropriate for this clinical application where highly flexible biodegradable materials are required because of the huge expansion ratio before and after deployment. One of the most practical strategies for tuning the properties of polymers is blending with another polymer or copolymerization. Copolymerization facilitates a broad range of properties, including good mechanical strength, biocompatibility, biodegradability, and processability, which makes them excellent materials for medical application.

In various embodiments, the biodegradable polymer is polycaprolactone (PCL), poly-(D,L-lactide-co-caprolactone) (PLC), poly-L-lactide (PLLA), poly-D-lactide (PDLA), polyglycolide (PGA), polylactic acid (PLA), poly-caprolactone-polylactic acid copolymer (PCL-PLA copolymer), polylactide-polyglycolide copolymer (PLGA), poly (trimethylene carbonate) (TMC); copolymers of polycaprolactone (PCL) and poly(trimethylene carbonate) (TMC); triblock copolymers of polylactic acid (PLA), polycaprolactone (PCL) and/or poly(trimethylene carbonate) (TMC); polylactic acid-polyethylene oxide copolymers, polygluconate polyhydroxybutyrate, polyanhydride, polyphosphoester, poly(amino acids), polydioxanone, cellulose, collagen, chitosan, or a mixture thereof.

In various embodiments, the biodegradable polymer comprises polycaprolactone (PCL), poly-(D,L-lactide-co-caprolactone) (PLC), polyglycolide (PGA), polylactic acid (PLA), polylactide-polyglycolide copolymer (PLGA), or a mixture thereof.

In various embodiments, the connecter 2 or the proximal junction portion 20 and the distal junction portion 30 may be made stiffer than the remainder of the device. Using different polymeric materials may also serve to alter the biodegradability of different portions of the device to result in a sequential degradation of different parts of the device. It is also possible to form all parts of the device from the same material but having specific thicknesses such that each part has the flexibility of stiffness required for its function.

Biodegradable polymers that are particularly suitable for use to form the proximal arms 11 and the distal arms 41 of the connector of the invention include polycaprolactone (PCL), poly-(D,L-lactide-co-caprolactone) (PLC), or a mixture thereof. In various embodiments, the proximal arms 11 consist of polycaprolactone (PCL), poly-(D,L-lactide-co-caprolactone) (PLC), or a mixture thereof. Polycaprolactone (PCL), poly-(D,L-lactide-co-caprolactone) (PLC), or their mixture are particularly suited to form the proximal and the distal arms 11, 41 due to their mechanical attributes such as flexibility and stiffness. Poly(D,L-lactide-co-caprolactone) (PLC) refers to a copolymer of poly(D,L-lactide) and poly (caprolactone), where the appropriate weight ratio of poly (D,L-lactide) to poly(caprolactone) in the copolymer may be in the range of about 1:1 to about 9:1, such as about 2:1, about 3:2, or about 7:3. In one embodiment, the weight ratio of poly(D,L-lactide) and poly(caprolactone) in the copolymer is about 7:3.

The connector may include poly-L-lactide (PLLA), poly-D-lactide (PDLA), polyglycolide (PGA), polylactic acid (PLA), polylactide-polyglycolide copolymer (PLGA), Polyethylene glycol (PEG), polyethylene oxide (PEO), diblock copolymers of Polyethylene glycol (PEG) and poly(lactic-co-glycolic acid) (PLGA), triblock copolymers of Polyethylene glycol (PEG) and poly(lactic-co-glycolic acid) (PLGA), diblock copolymers of polylactide (PLA) and polyethylene glycol (PEG), triblock copolymers of polylactide (PLA) and polyethylene glycol (PEG), or a mixture thereof. In various embodiments, the device comprises a biodegradable polymer as listed above. In various embodiments, the device consists essentially of the biodegradable polymer.

In various embodiments, the device, further comprises one or more plasticizer mixed with the biodegradable polymer. As used herein a "plasticizer" refers to an additive that increases the placicity or fluidity of a material, having a chemical structure that embeds between chains of the biodegradable polymer, spacing the units of the biodegradable polymer appart, and significantly lowering the glass transition temperature of the biodegradable polymer making it softer. The plasticizer includes a biodegradable compound such as acetylated monoglycerides or alkyl citrates. In various embodiments the plasticizer is selected from trioctyl citrate (TOC), trihexyl citrate (THC), triethyl citrate (TEC). Acetyl triethyl citrate (ATEC), tributyl citrate (TBC), acetyl tributyl citrate (ATBC), acetyl trioctyl citrate (ATOC), acetyl trihexyl citrate (ATHC), butyryl trihexyl citrate (BTHC), and trimethyl citrate (TMC). In various embodiments the plasticizer is trioctyl citrate (TOC), or trihexyl citrate (THC), In various embodiments, the connecter 2 or the proximal junction portion 20 and the distal junction portion 30 may be formed of a material having one or more plasticizer mixed with the biodegradable polymer. In various other embodiments, the arms 41, 11 may be formed of a material having one or more plasticizer mixed with the biodegradable polymer. In various other embodiments, the join between the arms and the connector may be formed of a material having one or more plasticizer mixed with the biodegradable polymer. It is also possible to form all parts of the device from the same material but having specific thicknesses such that each part has the flexibility of stiffness required for its function.

In various embodiments, the device, further comprises a film formed between the at least two proximal arms or the at least two distal arms whereby when the proximal arms or the distal arms are in the position in which the respective free ends of said proximal arms or distal arms is at an enlarged distance the film forms a disc shape.

In various embodiment where the device is made of a biodegradable polymer the at least two arms or can be stiffer than the film portions of the device by adjusting the thickness of the various parts.

In various embodiments the proximal arms 11 together with the film formed between the at least two proximal arms 12 forms a proximal support structure 10. Similarly, the distal arms 41 together with the film formed between the at least two distal arms 42 forms a distal support structure 40. The number of arms 11, 41 is not limited as long as they can anchor into the lumen. For example, in case the proximal support structure 10 comprises a connector film 12, the number of arms can include 2 or more arms as long as the proximal support structure 10 can support a proximal connector film 12. The proximal and/or the distal support structures 10, 40 may include, but are not limited to 2 to 8 arms 11, 41 or spokes, such as 2, 3, 4, 5, 6, 7, or 8 arms 11, 41 or spokes. The number of spokes in the proximal support structure 10 and in the distal support structure 40 may be the same or different. In various embodiments, the number of arms 11, 41 of the proximal and the distal support structure 10, 40 is the same, and contains four arms each.

In various embodiment, the outwardly extending arms 11, 41 of the proximal/distal support structure 10, 40 are spokes forming together with the connector film 12, 42, a disk-shaped connector structure. Disk-shaped means in the context of this application that the shape is like a circular disk, but can also be curved like a shell. Thus, the disc-shaped connector structure may be in any form between a disk and a half-shell. If the support structure and the connector film are in a half-shell, they look like an umbrella when connected to the longitudinal junction portion.

In this regard, the proximal/distal connector film 12, 42 may, in the context of the present application, be connected to the proximal support structure 10, 40, for example, by welding the film on the arms 11, 41. As an alternative to the welding of the film, the film may be glued, hot pressed, laminated or sewed to the arms 11, 41. In general one or more films may be used as the proximal connector film 12. For example, two, three, or four films may be provided on the proximal/distal support structure 10, 40 in a laminated structure.

In various embodiments, the proximal/distal support structure 10, 40 may be formed together with the proximal connector film 12 by solution casting in one or two consecutive steps. In one step, the arms 11, 41 are formed of the different material as the film 12, 42, so that the solvent used only dissolve the film not the arms. Thereby, an integrally formed as a disc comprising the proximal support structure 10 and the proximal connector film 12.

In various other embodiment, the proximal/distal connector film 12, 42 may extend between the arms 11, 41 of the support structure 10, 40. The term "extend" in the context of the present application means that the film extends from one arm to the proximate arm and can be spanned between the arms or spokes. Alternatively, the proximal/distal connector film 12/42 may be spanned over the proximal junction 20 end of the proximal support structure 10 or distal junction 30 end of the distal support structure 40, thereby forming the disk-shaped structure for anchoring the connector within the lumen.

The thickness of the connector films 12, 42 (if present) may be at least about 10, 20, 30, 40, 50, 60, 70, 80, 90, 100, 110, 120 µm but below 500, 450, 400, 350, 300, 250, 200, 190, 180, 170, 160, 150 µm as long as the material has a suitable flexibility to be moved or folded during the deployment procedure.

Figure 2:
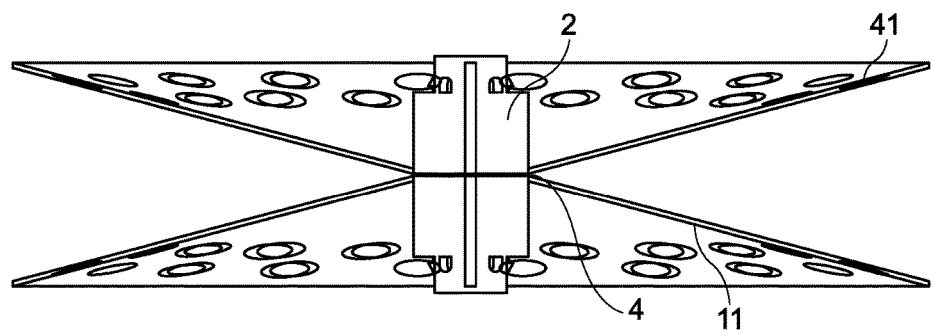
FIG. 2: shows a perspective view of (a) a connector according to an embodiment and (b) a connector according to another embodiment in a disconnected state.
Figure 2:
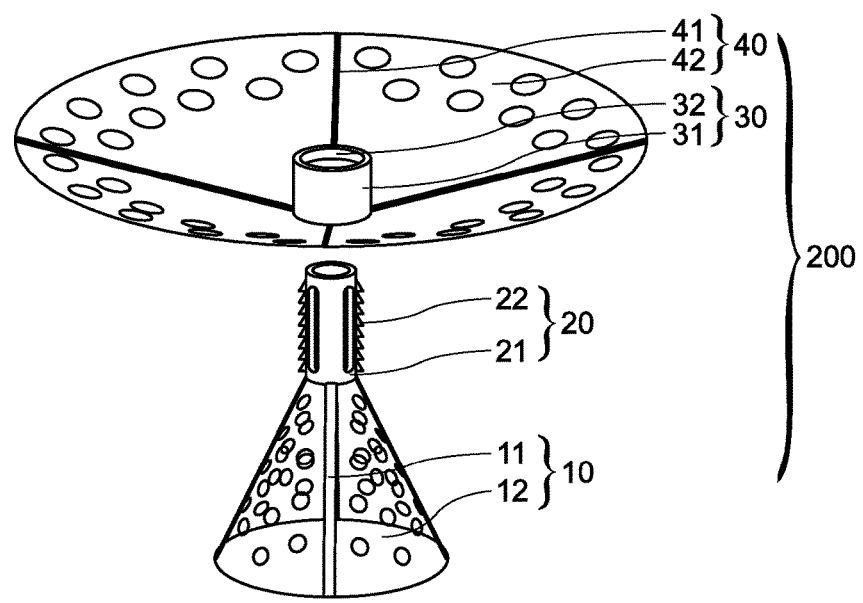

An embodiment is depected in FIG. 2 whereby, a connector (200) comprises a proximal support structure (10), a proximal junction portion (20), a distal junction portion (30) and a distal support structure (40). The proximal support structure (10) comprises the at least two arms, in the form of a plurality of spokes (11) outwardly extending from the proximal junction portion (20). In the embodiment shown, a proximal connector film (12) is supported by the proximal spokes (11), whereby the proximal connector film (12) is expanded between the spokes (11) of the proximal support structure (10). The distal support structure (40) comprises at least two arms, in the form of a plurality of spokes (41) outwardly extending from a distal junction portion (30). The proximal junction portion (20) comprises a proximal hollow tube (21) and a proximal structured surface (22), the distal junction portion (30) comprises a distal hollow tube (31) and a distal structured surface (32), connects the proximal support structure (10) with the distal support structure (40).

Figure 3:
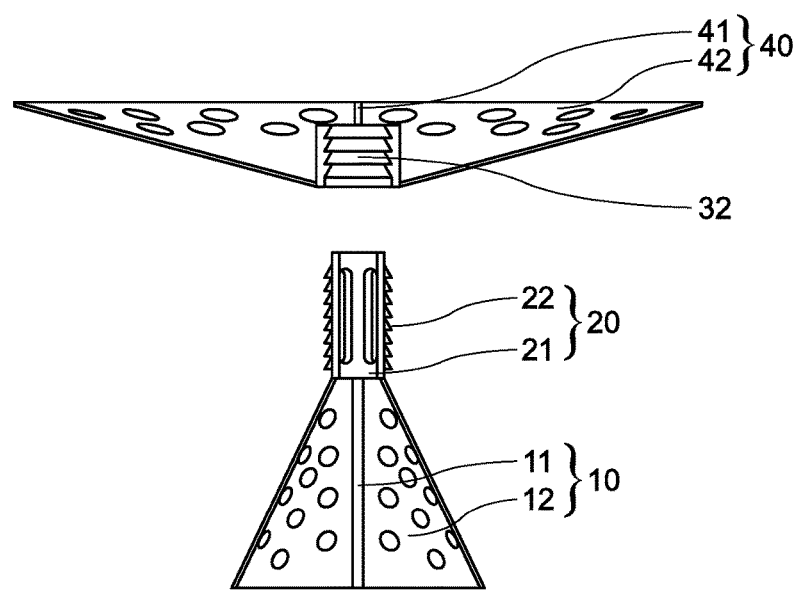
FIG. 3: shows a cross-section view of a connector according to an embodiment in a disconnected state.
Figure 4:
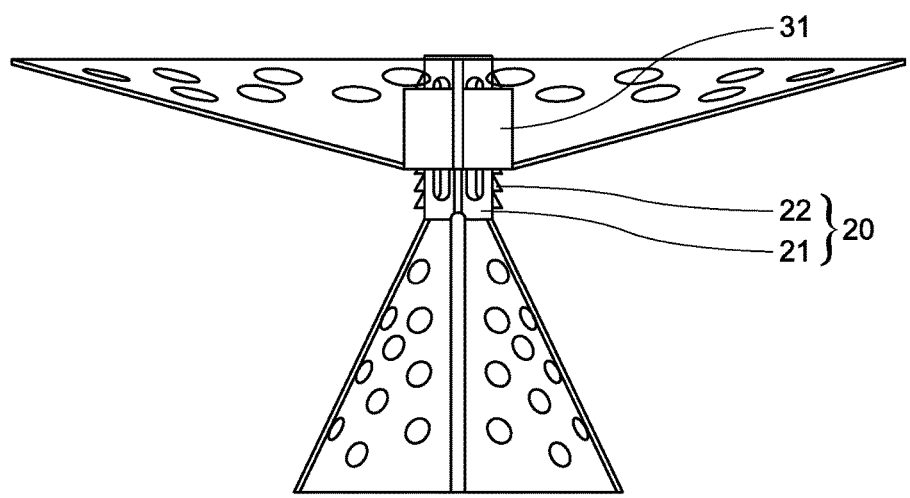
FIG. 4: shows a perspective view of a connector according to an embodiment in a connected state.
Figure 5:
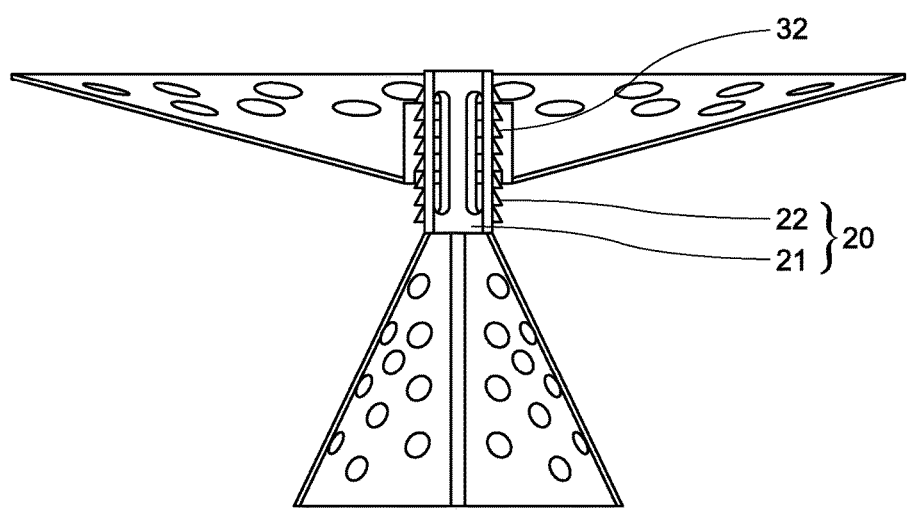
FIG. 5: shows a cross-section view of a connector according to an embodiment in a connected state.

In FIG. 3 the proximal junction portion (20) comprises a proximal hollow tube (21) and expansion bolt chamfered exterior surface (22), the distal junction portion (30) comprises a distal hollow tube (31) and an expansion bolts chamfered interior surface (32).

In various embodiments the device further comprises one or more therapeutically active agent.

The term "therapeutically active agent" generally means a therapeutic or pharmaceutical agent which may be mixed into the polymer composition, or impregnated or incorporated into the device.

The therapeutic agent may be any therapeutic or pharmaceutical agent suitable for use in drug-containing materials for the devices. Various examples include, but are not limited to antibiotics such as dactinomycin (actinomycin D) daunorubicin, doxorubicin and idarubicin), anthracyclines, mitoxantrone, bleomycins, plicamycin (mithramycin) and mitomycin, enzymes (L-asparaginase); antiproliferative/antimitotic agents including natural products, such as vinca alkaloids (e.g. vinblastine, vincristine, and vinorelbine), paclitaxel, epidipodophyllotoxins (e.g. etoposide, teniposide), antiproliferative/antimitotic alkylating agents such as nitrogen mustards (such as mechlorethamine, cyclophosphamide and analogs, melphalan, chlorambucil), ethylenimines and methylmelamines (hexamethylmelamine and thiotepa), alkyl sulfonates-busulfan, nirosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (e.g. estrogen); anticoagulants (heparin, synthetic heparin salts and other inhibitors of thrombin); fibrinolytic agents (such as tissue plasminogen, activator, streptokinase and urokinase); antiplatelet (such as aspirin, dipyridamole, ticlopidine, clopidogrel, abciximab); antimigratory; antisecretory (such as breveldin); antiinflammatory: such as adrenocortical steroids (cortisol, cortisone, fludrocortisone, prednisone, prednisolone, 6-alpha-methylprednisolone, triamcinolone, betamethasone, and dexamethasone), non-steroidal agents (such as salicylic acid derivatives e.g. aspirin); para-aminophenol derivatives (e.g. acetaminophen); indole and indene acetic acids (such as indomethacin, sulindac, and etodalac), heteroaryl acetic acids (such as tolmetin, diclofenac, and ketorolac), arylpropionic acids (such as ibuprofen and derivatives), anthranilic acids (such as mefenamic acid, and meclofenamic acid), enolic acids (such as piroxicam, tenoxicam, phenylbutazone, and oxyphenthatrazone), nabumetone, gold compounds (such as auranofin, aurothioglucose, gold sodium thiomalate); immunosuppressive (such as cyclosporine, tacrolimus (FK-506), sirolimus (rapamycin), azathioprine, mycophenolate mofetil); angiogenic such as vascular endothelial growth factor (VEGF), fibroblast growth factor (FGF); nitric oxide donors; antisense oligo nucleotides and combinations thereof.

The therapeutic agent may include, but is not limited to, a drug, an antibiotic, an anti-inflammatory agent, an anti-clotting factor, a hormone, a nucleic acid, a peptide, a cellular factor, a growth factor, a ligand for a cell surface receptor, an anti-proliferation agent, an anti-thrombotic agent, an antimicrobial agent, an anti-viral agent, a chemotherapeutic agent, or an anti-hypertensive agent to improve the sealing effect, the healing process, or preventing thrombi, for example.

In this context, it is noted that the therapeutically active agent to be incorporated into one or more polymeric materials of the connector may be a drug, a protein, a growth factor, or combinations thereof.

The term "drug" generally means a therapeutic or pharmaceutical agent which may be included/mixed into the biodegradable polymer, impregnated, dispersed within or dissolved into the biodegradable polymer in order to provide a drug-eluting composition. The term "protein" is meant any naturally occurring polypeptide that comprises more than 40 amino acid residues. The protein may be a full length protein or a truncated form, for example, an active fragment. Illustrative examples of proteins include, but are not limited to antibodies or other binding proteins with antibody like properties (for example, affibodies or lipocalin muteins knows as "Anticalins®") for selected cell receptors, growth factors such as VEGF (Vascular. Endothelial Growth Factor) and similar factors for transmitting signals, cardiovascular therapeutic proteins or cardiac hormones and active fragments thereof or prohormones or preprohormones of such cardiac hormones (these hormones or the prohormones can either be peptides as defined herein, if they have less than 40 amino acid residues of a protein, should there polypeptide sequence contain more the 40 amino acid residues). Further examples for cardiovascular therapeutic agents can be peptides or DNA such as the DNA for nitric oxide. Examples of nucleic acid molecules include sense or anti-sense DNA molecules (if expression of a target gene is to be controlled) or the coding sequence (either alone or in gene-therapy vector, for example) of a therapeutically active protein that is to be produced. In such a case, the nucleic acid may code for a protein that promotes wound healing as described in. International patent application WO 97/47254, for example.

The therapeutically active agent may be dispersed within or dissolved in the biodegradable polymer used to form the connector of the first aspect. For example, the drug may be present as particles within a polymeric matrix formed from the biodegradable polymer. In other embodiments, the drug may first be dissolved in the polymeric blend, prior to use of the polymeric blend to form the connector. In various embodiments, the drug is homogeneously dispersed within or dissolved in the biodegradable polymer, such that drug elution from the connector is at least substantially uniform. The release of the drug from the connector may also be accomplished by controlled degradation of the biodegradable polymer. After drug elution, the biodegradable polymer may be biodegraded within the body in order to avoid any deleterious effects generally associated with decomposition reactions of polymer compounds in vivo.

All therapeutically active agents mentioned above can be used alone or in any combination thereof in the polymer material of this embodiment. The amount of the therapeutically active agent (or 2 or more agents together) in the polymeric material is not limited and can be as high as wanted as long as the physical properties of the polymer material, especially the glass transition temperature and the melting temperature, are not adversely affected. In some embodiments, the amount of the therapeutically active agent, based on the dry weight of the polymer material that contains the agent, may be up to about 35 wt %. The therapeutically active agent may be present in an amount of 0.1 to 35 wt %, 1 to 35 wt % or 1 to 10, 15, 20, 25 or 30 wt % based on the dry weight of the polymer material that contains the drug. In this context, it is again noted that it is possible to include more than one therapeutically active agent of the same or different type into a polymer material of the films or the supports, for example, an antibiotic drug and an anti-inflammatory drug or an anti-thrombotic drugs.

The device in various embodiments can thereby degrade at a controllable rate in a desired time and elute an antibiotic compound/anticancer drugs at a precisely-controlled rate such that it minimizes the chances of infection and cancer recurrence.

In various embodiments the device may further comprises a radiopacifier deposited therein. One or more elements selected from the group of the proximal support structure 10, the distal support structure 40, the proximal junction portion 20, the distal junction portion 30, the proximal connector film 12, and the distal connector film 42, may comprise a radiopacifier deposited at its surface and/or blended in the material of which the elements comprise. For example, the radiopacifier may be present in the proximal, distal support structures 10, 40 of the device.

The radiopacifier may for example be a material including metals, metal oxides or metal salts, such as gold particles, bariums salts or bismuth glasses, for example, but are not limited to these examples. In the present embodiment, the radiopacifier may comprise or consists of barium sulfate ($BaSO_4$). In the films, the radiopacifier may be incorporated into the polymeric material by solution casting or extruder mixing in an amount of more than 0.1, 0.2, 0.3, 0.4, 0.5, 1.0, 1.5, 2.0, 2.5, 3.0, 3.5, 4.0 wt % to less than 40, 35, 30, 25, 20, 15, 10, 9, 8, 7, 6, 5 wt % as long as the films are provided with radio-opacity for making the device visible by means of fluoroscopy, for example, during the deployment procedure.

In the films 12, 42, the radiopacifier may often be less concentrated compared to the arms 11,41 to avoid any affecting of the physical properties of the polymers or copolymers. In other parts of the connector, for example in the junction portion 2, 20, 30 or the proximal or distal arms 11,41, the amount of radiopacifier may be increased because a higher stiffness of the junction portion or the arms is suitable and the visibility of the connector may simultaneously be improved. For example, varying amounts of $BaSO_4$ may be used in various parts of the connector to enhance stiffness and non-stickiness. The proximal connector films 12, 42 of the device may, for example, be solution casted or hot-pressed with an amount of $BaSO_4$ ranging from about 0 wt % to about 40 wt %. The junction portion may, for example, be made of a biodegradable polymer having about 0 wt % to about 40 wt % $BaSO_4$. Either or both the proximal and the distal support structures 10, 40 may, on the other hand, contain about 1 wt % to about 40 wt % $BaSO_4$.

In various embodiments the device may further comprising a hollow tubular sheath slidable over the hollow connector when the proximal arms are in a position in which the free ends of said proximal arms are closer to each other or the distal arms are in a position in which the free ends of said distal arms are closer to each other.

The sheath is able to hold the arms 41, 11 flat or parallel along the hollow connector 2 by providing pressure on the arms.

Another aspect of the invention relates to a method of forming an anastomotic joint between two parts of a human or animal body using a device of claim 1 comprising:
  a) Providing pressure to move the proximal arms into a position in which the free ends of said proximal arms are closer to each other;
  b) Providing pressure to move the distal arms into a position in which the free ends of said distal arms are closer to each other;
  c) Pushing the device using the distal end leading into a passage in the first human or animal body part until the distal arms are located in the first lumen of the first body part;
  d) Releasing the pressure on the distal arms allowing them to move to the biased position in which the respective free ends of distal arms is at an enlarged distance to urge against the first lumen of the first body part;
  e) Pushing the device using the proximal end leading into a passage in the second human or animal body part until the proximal arms are located in the second lumen of the second body part; and
  f) Releasing the pressure on the proximal arms allowing them to move to the biased position in which the respective free ends of said proximal arms is at an enlarged distance to urge against the second lumen of the second body part.

In various embodiments where the hollow connector comprises two interconnecting parts, a proximal connector portion and a distal connector portion, the proximal connector portion is connected to the distal connector portion after step f.

Figure 6:
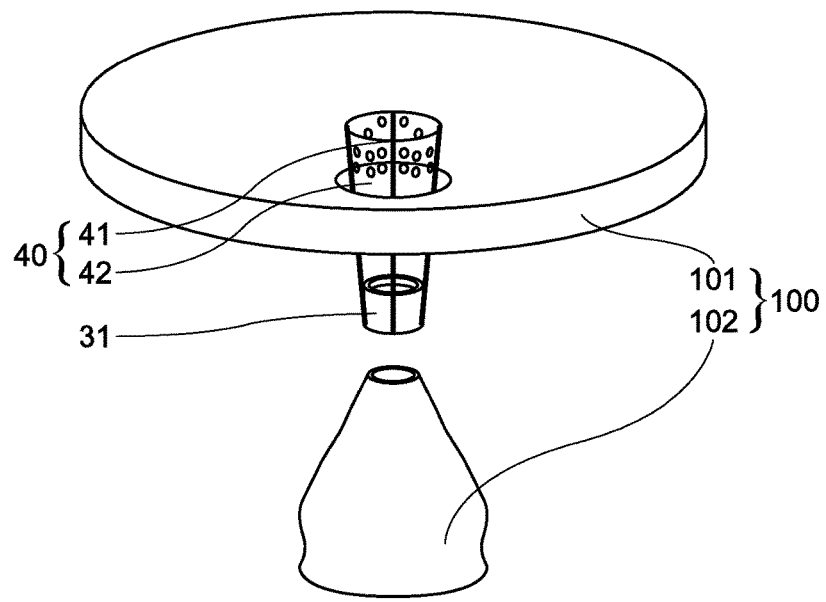
FIG. 6: shows a perspective view of a connector according to an embodiment in a mode of use.
Figure 7:
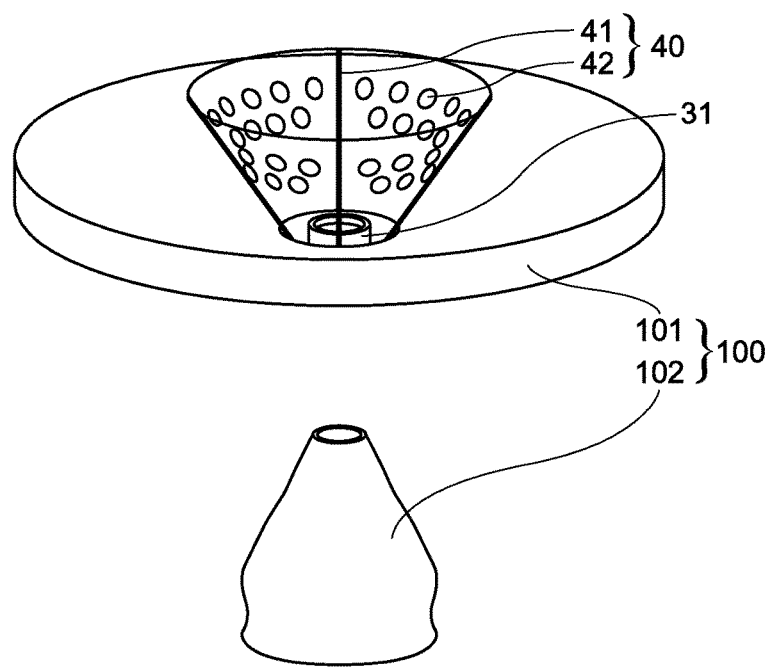
FIG. 7: shows a perspective view of a connector according to an embodiment in a mode of use.
Figure 8:
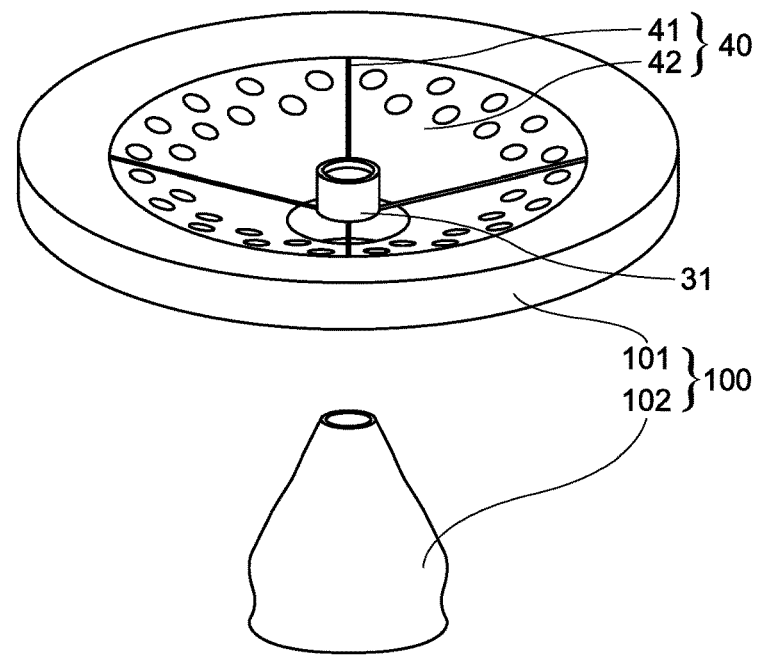
FIG. 8: shows a perspective view of a connector according to an embodiment in a mode of use.
Figure 9:
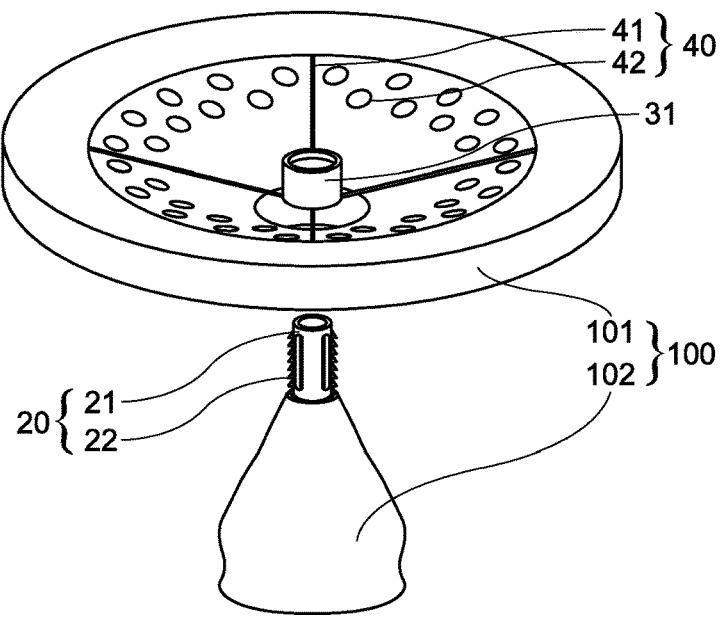
FIG. 9: shows a perspective view of a connector according to an embodiment in a mode of use.
Figure 10:
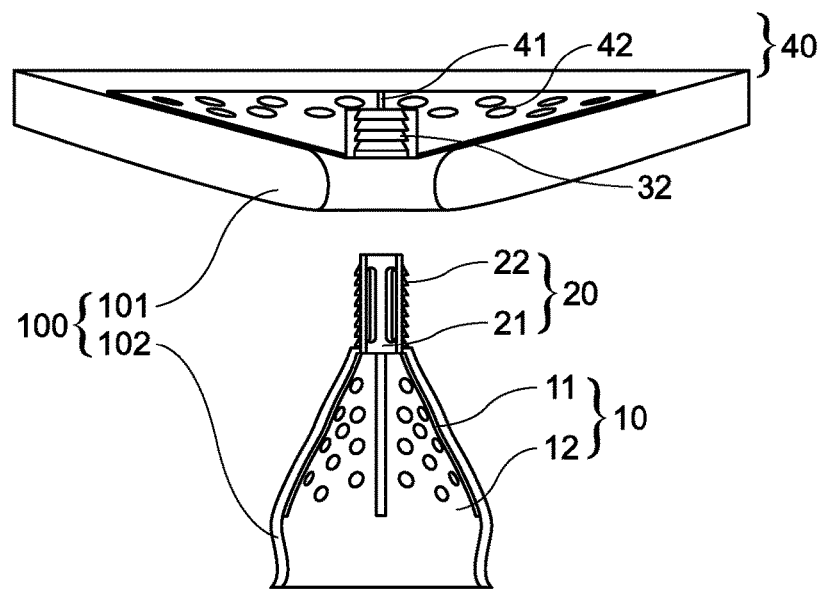
FIG. 10: shows a cross-section view of a connector according to an embodiment in a mode of use.
Figure 11:
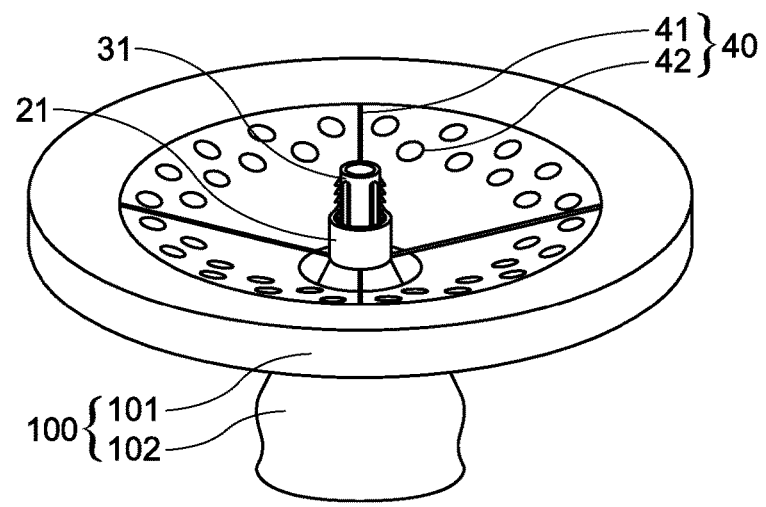
FIG. 11: shows a perspective view of a connector according to an embodiment in a mode of use.

In the FIG. 1 (b), 100 denotes the gap between two disconnected hollow parts of body whereby (101) denotes the second lumen and (102) denotes the first lumen. As seen from FIGS. 6 and 7, the distal support structure (40) is moved through the opening of the first lumen (102). In FIG. 7, the distal support structure (40) of the connector and the distal junction portion (30) are released out of the pressure through the opening on the second lumen (101). In FIG. 7, the distal support structure (40) of the connector is anchored and immobilized within the second lumen (101). In FIG. 9, the proximal junction portion (20) of the connector is inserted through the opening of the first lumen (102). Then in FIG. 11, the proximal junction portion (20) of the connector is connected with the distal junction portion (30) of the connector.

Figure 12:
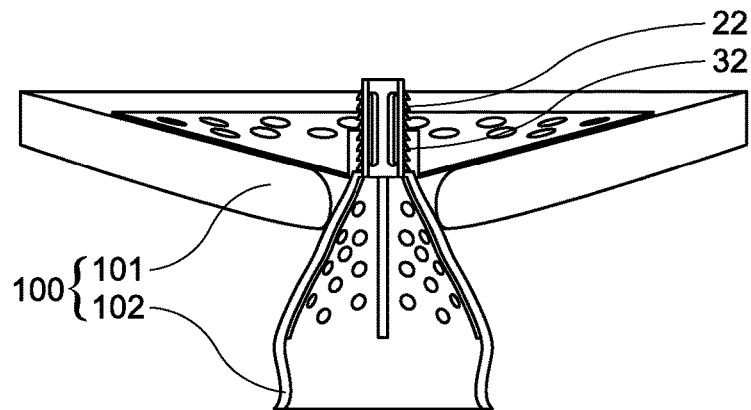
FIG. 12: shows a cross-section view of a connector according to an embodiment in a mode of use.
Figure 13:
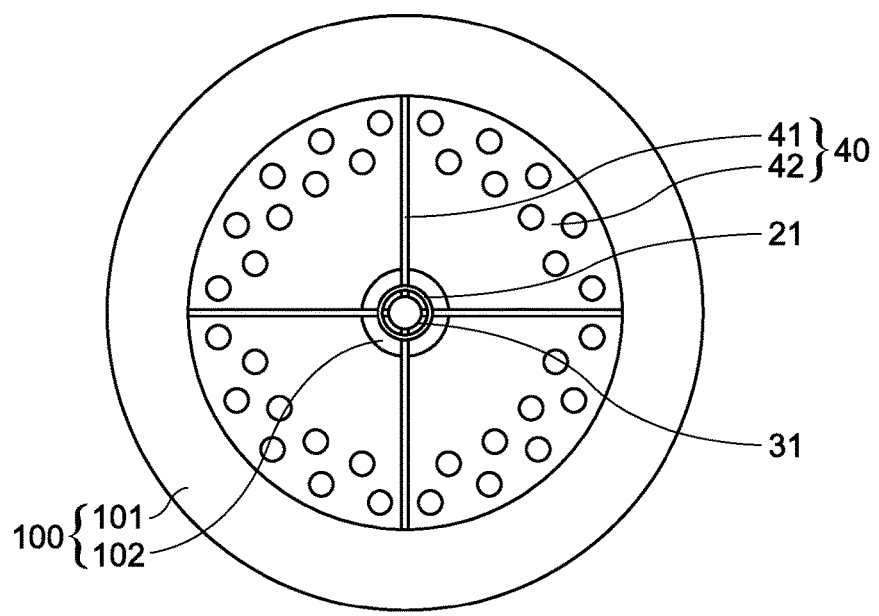
FIG. 13: shows the plan view of the connector looking from the inside of the first lumen.

FIG. 12 shows a cross-section view of a connector with the proximal junction portion (20) of the connector is connected with the distal junction portion (30) of the connector, to create the anastomotic joint of the second lumen (101) and the first lumen (102).

Figure 14:
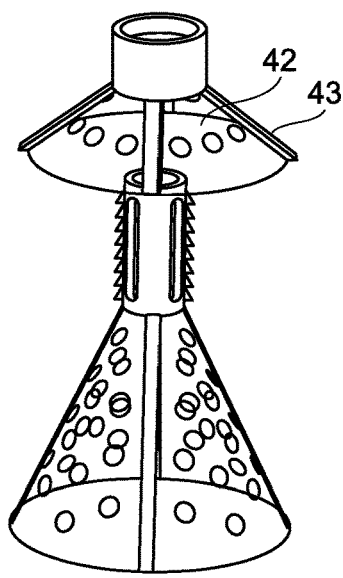
FIG. 14: shows a perspective view of a connector according to another embodiment of the invention in a disconnected state.
Figure 16:
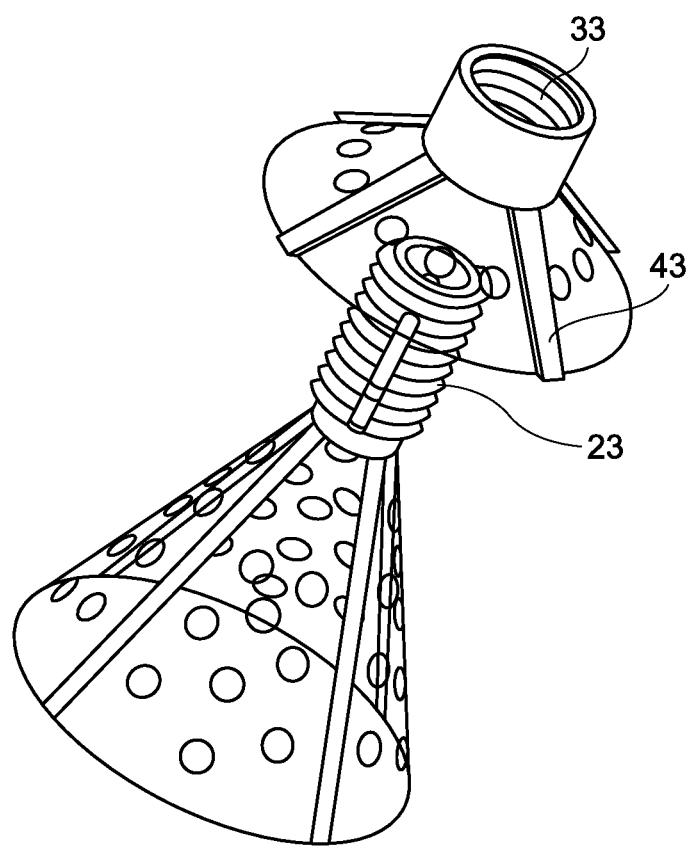
FIG. 16: shows a perspective view of a connector according to another embodiment of the invention in a disconnected state.

In FIGS. 14 and 16 the arms (43) of the distal support structure (40) outwardly extend away from a direction of the distal junction portion (30). In the embodiment shown, a distal connector film (42) is supported by the distal arms (43), whereby the distal connector film (42) is expanded between the arms (43) of the distal support structure (40). A screw threaded exterior surface (23) of the proximal junction portion (20) and a screw threaded interior surface (33) of the distal junction portion (30) is shown.

Figure 15:
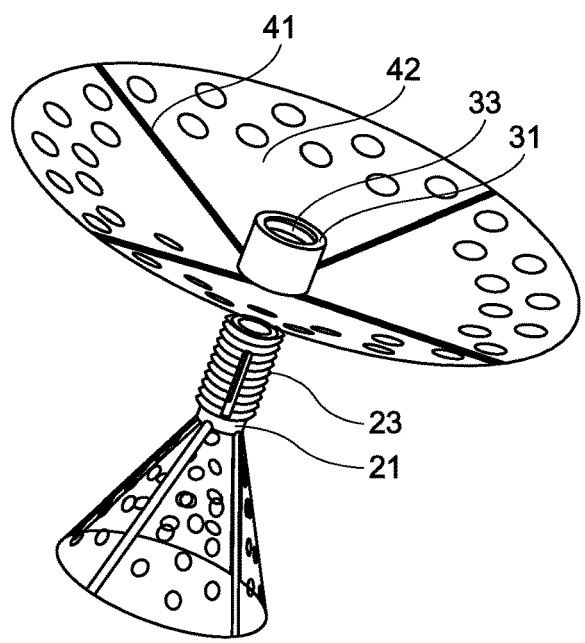
FIG. 15: shows a perspective view of a connector according to another embodiment of the invention in a disconnected state.

In FIG. 15 the arms (41) of the distal support structure (40) outwardly extend in direction of a distal junction portion (30). A screw threaded exterior surface (23) of the proximal junction portion (20) and a screw threaded interior surface (33) of the distal junction portion (30) is shown.

The term 'pressure' refers to any pressure that is able to overcome the bias of the at least two arms in the open position in which the respective free ends of the arms is at an enlarged distance. In various embodiments the pressure is provided by the surgeons hand or by a tied suture or band or sheath. In various embodiments the pressure is provided by a hollow tubular sheath slidable over the hollow connector when the proximal and distal arms are folded towards the hollow connector.

In various embodiments the method may further comprise delivering one or more therapeutically active agent to the anastomotic joint at a measured release rate by incorporating the one or more therapeutically active agent into a biodegradable polymer and making a part of the device from the biodegradable polymer containing the one or more therapeutically active agent.

In various embodiments the method may further comprise visualizing the device in situ with electromagnetic radiation whereby the device further comprises a radiopacifier deposited therein. Methods of detecting radiopacific material with electromagnetic radiation may be done using methods known in the art.

Exemplary Embodiments

Forming an anastomotic joint between the bladder and urethra after prostate removal.

Surgical removal of the prostate is one of two main treatments for prostate cancer. In addition to the open surgery, a few new types of surgery such as laparoscopic prostatectomy and robotic-assisted prostatectomy were also developed in recent years. However, the sewing is still required for the anastomotic joint following surgical removal of the prostate, and is technically challenging with a long catheterization period.

The biodegradable connector has several advantages. A key advantage is that the connector will result in quick creation of the anastomotic joint, without the stitching. This greatly improves the healing of the anastomosis in the gap between the bladder and urethra, reduces the catheterization time for the patient and increases the post-operative security for the patient, and enhances the quality of life for many current and future patients. Second key advantage is the ability of biodegradable materials (polymers) to elute therapeutic drugs directly to the affected area over time, to prevent infection and cancer recurrence; the local delivery circumvents issues relating to systemic drug administration and patient compliance. Third key advantage, the proposed connector is self-expandable with a unique flap design, and can be deployed using currently-available interventional delivery system, which is familiar to both the urologist and all interventional clinicians.

Prostate Cancer is the third leading cause of cancer in Singapore men and the sixth leading cause of cancer death in 2011 among men worldwide. The prototype device can be easily deployed by the urologist following surgical removal of the prostate. The number of other procedures that will utilize this new concept is high including removal of any part of the gastrointestinal tract, resection of the pancreas or reconnection of vascular vessels such us in bibass operations.

The prostate is a small, walnut-sized structure that makes up part of a man's reproductive system. It wraps around the urethra, the tube that carries urine out of the body.

Prostate cancer is cancer that starts in the prostate gland. It is the most common diagnosed disease in men over the age of fifty [10]. Rates of detection vary widely across the world, it is most common in the developed world with increasing rates in the developing world [7], with South and East Asia detecting less frequently than in Europe, and especially the United States [9]. The prostate cancer was the sixth leading cause of cancer death in 2011 among men worldwide[1]; second leading cause of cancer death in the United States; third leading cause of cancer death in Singapore men.

This prototype will make the robotic surgery a smoother experience and less time-consuming.

The connector used was a catheter-deliverable device that creates the anastomotic joint like a gap in the ureteric system to create the anastomotic joint for a gap between the bladder and the urethra after prostate removal. Once in place, the proximal portion of the connector is released in the urethra, and the distal portion of the connector is released in the bladder from the sheath respectively. A proximal connector film was supported by the proximal support structure, which anchored and immobilized within the urethra when the proximal support structure was deployed. A distal connector film was supported by the distal support structure, which anchored and immobilized within the bladder when the distal support structure was deployed. The deployed proximal support structure connected with the deployed distal support structure through the proximal junction portion and the distal junction portion connecting, to create the anastomotic joint of the bladder and the urethra.

The connector comprises a proximal support structure comprising four arms; a distal support structure comprising at four arms.

The connector comprises a proximal junction portion and a distal junction portion adapted for connecting the proximal support structure with the distal support structure. In this embodiment, the proximal junction portion is the proximal hollow tube with the expansion bolts chamfered exterior surface, and the distal junction portion is the distal hollow tube with expansion bolts chamfered interior surface The connector further comprises connector films between the arms. In this embodiment, the arms of the proximal support structure support a proximal connector film. While the arms of the distal support structure also support a distal connector film. The connector consists essentially of a biodegradable polymer. In various embodiments, the proximal support structure, the distal support structure, the proximal junction portion, the distal junction portion, the proximal connector film and the distal connector film consist essentially of a biodegradable polymer.

The proximal support structure and the distal support structure of the connector of the invention include a mixture of polycaprolactone (PCL), and poly-(D,L-lactide-co-caprolactone) (PLC), where the appropriate weight ratio of poly (D,L-lactide) to poly(caprolactone) in the copolymer was about 7:3.

The junction portion of the connector included a mixture polyglycolide (PGA), polylactic acid (PLA), and polylactide-polyglycolide copolymer (PLGA).

The arms of the proximal support structure were adapted to provide anchorage for the device in the urethra by outwardly extending from the proximal junction portion and contacting the lumen wall. In so doing, upon deployment of the proximal support structure in the urethra, pressure exerted by the proximal support structure on the lumen walls serves to keep the proximal portion of the connector in place. In embodiments wherein the lumen is urethra, for example, the proximal support structure of the connector is contained in its entirety within the urethra such that the proximal end of the connector anchors in the urethra.

The arms of the distal support structure were adapted to provide anchorage for the connector in the second lumen by outwardly extending from the distal junction portion and contacting the second lumen wall in the bladder. In so doing, upon deployment of the distal support structure in the lumen, pressure exerted by the distal support structure on the lumen walls serves to keep the distal portion of connector in place. In embodiments wherein the lumen is the bladder, for example, the distal support structure of the connector is contained in its entirety within the bladder such that the distal end of the connector anchors in the bladder.

The proximal junction portion, and the distal junction portion included a material comprising a therapeutically active agent. The therapeutically active agent was encapsulated in nonprous microparticles of PLGA (75:25, lactide glycolide). The therapeutic agent was a combination of paclitaxel, and prednisone in equal amounts of 20, 25 and 30 wt % based on the dry weight of the polymer material. These encapsulated microparticles were then mixed with the other copolymers used to form the proximal junction portion, and the distal junction portion. The final concentration of therapeutically active agent was in an amount of 5, 10 and 15 wt % based on the dry weight of the copolymer material.

Radiopacifier material of barium sulfate ($BaSO_4$) was incorporated into the polymeric material by solution casting or extruder mixing in an amount of 20 wt % in the junction portion.

A connector for general use in the anastomosis of body ducts, vessels, organs, and other structures, collectively body lumens. The connector comprises:
  a) a proximal support structure comprising at least two arms; wherein the arms serve to anchor and immobilize the proximal end of connector within the first lumen;
  b) a distal support structure comprising at least two arms, wherein the arms serve to anchor and immobilize the distal end of connector within the second lumen;
  c) a proximal junction portion comprising a proximal hollow tube and a proximal structured surface;
  d) a distal junction portion comprising a distal hollow tube and a distal structured surface, wherein the junction portion serve to connect the proximal support structure and the distal support structure of connector, and to create the anastomotic joint of the first lumen and the second lumen, wherein the connector consists essentially of a biodegradable polymer, wherein the proximal support structure and the distal support structure comprise or consist of polycaprolactone (PCL), poly-(D,L-lactide-co-caprolactone) (PLC), or a mixture thereof; the junction portion comprise or consist of polyglycolide (PGA), polylactic acid (PLA), polylactide-polyglycolide copolymer (PLGA), or a mixture thereof.

A method for creating the anastomotic joint of body ducts, vessels, organs, and other structures, collectively body lumens. The method comprising:
 a) providing a sheath into which an connector according to the first aspect has been inserted;
 b) moving the sheath containing the connector through the opening on the first lumen, and the opening on the second lumen;
 c) pushing the distal support structure of the connector out of the sheath through the opening on the second lumen;
 d) releasing the distal support structure in the second lumen to anchor and immobilize the distal end of connector within the second lumen;
 e) withdrawing the sheath to release a proximal support structure of the connector in the first lumen to anchor and immobilize the proximal end of connector within the first lumen; and
 f) connecting the proximal end of the connector in first lumen and the distal end of the connector in the second lumen through the junction of the connector to create the anastomotic joint of the first lumen and the second lumen,
 wherein the connecting is through either the screw thread or the expansion bolts chamfers of the junction part of the connector.

Use of a connector according to the first aspect or a method according to the second aspect for creating the anastomotic joint of the bladder and the urethra.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically, recited herein.

Other embodiments are within the following claims and non-limiting examples. In addition, where features or aspects of the invention are described in terms of groups, those skilled in the art will recognize that the invention is also thereby described in terms of any individual member or subgroup of members of the group.

The invention claimed is:

1. A device for forming an anastomotic joint between two parts of a human or animal body comprising: a hollow connector comprising two interconnecting parts, a proximal hollow tube and a distal hollow tube, wherein the proximal hollow tube having directly connected to a first end of the proximal hollow tube at least two proximal arms each of which has a free end, wherein at least portions including the respective free ends of these at least two proximal arms are movable or rotatable or foldable with regard to each other between positions in which the free ends of said proximal arms are closer to each other and positions in which the distance between the free ends of said proximal arms is comparably larger, and wherein these at least two proximal arms are biased towards respective directions in which the respective free ends of said proximal arms are movable to respective positions in which the distance between said free ends of said proximal arms is enlarged, so that the proximal arms are configured to urge against an inner wall surface of a first lumen of a first human or animal body part so as to anchor the connector to said first human or animal body part, wherein the distal hollow tube having directly connected to a first end of the distal hollow tube at least two distal arms each of which distal arms has a free end, wherein at least portions including the respective free ends of these at least two distal arms are movable or rotatable or foldable with regard to each other between positions in which the free ends of said distal arms are closer to each other and positions in which the distance between the free ends of said distal arms is comparably larger, and wherein these at least two distal arms are biased towards respective directions in which the respective free ends of said distal arms are movable to respective positions in which the distance between said free ends of said distal arms is enlarged, so that the distal arms are configured to urge against an inner wall surface of a second lumen of a second body part so as to anchor the connector to said second human or animal body part, and wherein the proximal hollow tube and the distal hollow tube are configured to interconnect with each other such that the distal hollow tube surrounds the proximal hollow tube, and both the proximal hollow tube and the distal hollow tube are oriented with the first end of the proximal hollow tube and the first end of the distal hollow tube directed towards a same direction.

2. The device of claim 1, wherein a surface of an inner wall of the distal hollow tube comprises grooves patterned on the surface; and a surface of an outer wall of the proximal hollow tube comprises projections patterned on the surface whereby the projections are able to interlock with the grooves forming the interconnected parts of the hollow connector.

3. The device of claim 2, wherein the grooves are a thread track and the projections are a thread whereby the two parts are interconnected by screwing the proximal hollow tube and the distal hollow tube together.

4. The device of claim 2, wherein the grooves are sleeves and the projections are expansion-bolts whereby the two parts are interconnected by forcing the proximal hollow tube over the distal hollow tube.

5. The device of claim 1, wherein the device comprises a biodegradable polymer.

6. The device of claim 5, wherein the biodegradable polymer comprises polycaprolactone (PCL), poly-(D,L-lactide-co-caprolactone) (PLC), polyglycolide (PGA), polylactic acid (PLA), polylactide-polyglycolide copolymer (PLGA), or a mixture thereof.

7. The device of claim 1, further comprising one or more plasticizers.

8. The device of claim 1, further comprising a film formed between the at least two proximal arms or the at least two distal arms whereby when the proximal arms or the distal arms are in the position in which the respective free ends of said proximal arms or distal arms are at an enlarged distance, the film forms a disc shape.

9. The device of claim 1, further comprising one or more therapeutically active agents.

10. The device of claim 1, further comprising a radiopacifier deposited therein.

11. The device of claim 1, further comprising a hollow tubular sheath slidable over the hollow connector when the proximal arms or distal arms are in a position in which the free ends of said proximal arms or said distal arms are closer to each other.

12. A method of forming an anastomotic joint between two parts of a human or animal body using the device of claim 1, the method comprising:
 a. providing pressure to move the proximal arms into a position in which the free ends of said proximal arms are closer to each other;
 b. providing pressure to move the distal arms into a position in which the free ends of said distal arms are closer to each other;
 c. pushing the device using the distal end leading into a passage in the first human or animal body part until the distal arms are located in the first lumen of the first body part;
 d. releasing the pressure on the distal arms allowing them to move to the biased position in which the respective free ends of the distal arms is at an enlarged distance to urge against the first lumen of the first body part;
 e. pushing the device using the proximal end leading into a passage in the second human or animal body part until the proximal arms are located in the second lumen of the second body part; and
 f. releasing the pressure on the proximal arms allowing them to move to the biased position in which the respective free ends of the proximal arms is at an enlarged distance to urge against the second lumen of the second body part.

13. The method of claim 12, wherein the hollow connector comprises two interconnecting parts, a proximal connector portion and a distal connector portion, whereby the proximal connector portion is connected to the distal connector portion after step f.

14. The method of claim 12, wherein the pressure is provided by a hollow tubular sheath slidable over the hollow connector when the proximal arms or distal arms are in a position in which the free ends of said proximal arms or said distal arms are closer to each other.

15. The method of claim 12, further comprising: delivering one or more therapeutically active agents to the anastomotic joint at a measured release rate by incorporating the one or more therapeutically active agents into a biodegradable polymer; and making a part of the device from the biodegradable polymer containing the one or more therapeutically active agents.

16. The method of claim 12, further comprising visualizing the device in situ with electromagnetic radiation, whereby the device further comprises a radiopacifier deposited therein.

\* \* \* \* \*